| United States Patent [19] | [11] Patent Number: 4,596,831 |
| Hsu et al. | [45] Date of Patent: Jun. 24, 1986 |

[54] POLYMER BOUND FISCHER-TROPSCH CATALYSTS

[75] Inventors: Wen-Liang Hsu, Copley; Richard J. Kurr, Akron; Neil A. Maly, Tallmadge; Dane K. Parker, Massillon; Robert W. Strozier, Akron, all of Ohio

[73] Assignee: The Goodyear Tire & Rubber Company, Akron, Ohio

[21] Appl. No.: 773,958

[22] Filed: Sep. 9, 1985

Related U.S. Application Data

[62] Division of Ser. No. 631,698, Jul. 17, 1984.

[51] Int. Cl.$^4$ .............................................. C07C 1/04
[52] U.S. Cl. .................................... 518/715; 518/716; 518/717; 518/719; 518/721; 518/728; 502/159; 502/153
[58] Field of Search ............... 518/715, 716, 717, 719, 518/721, 728

[56] References Cited

U.S. PATENT DOCUMENTS

| 4,179,402 | 12/1979 | Kim et al. ........................... 518/715 |
| 4,179,403 | 12/1979 | Kim et al. ........................... 518/715 |
| 4,230,633 | 10/1980 | Vollhardt et al. .................. 518/715 |

OTHER PUBLICATIONS

Benner et al., ACS Symposium Series 152 (1981), pp. 165–189.

*Primary Examiner*—Howard T. Mars
*Attorney, Agent, or Firm*—D. O. Nickey

[57] ABSTRACT

There is disclosed a resin-metal (complex) catalyst, a method for its preparation, activation and use in carrying out Fischer-Tropsch reactions. The complex is a resin which has attached to it a coordination compound(s) and a metal(s). The complex has utility as a Fischer-Tropsch catalyst. More specifically, the complex is useful for the gaseous conversion of synthesis gas (carbon monoxide and hydrogen) to hydrocarbons.

4 Claims, No Drawings

POLYMER BOUND FISCHER-TROPSCH CATALYSTS

This is a divisional of application Ser. No. 631,698, filed July 17, 1984.

TECHNICAL FIELD

This invention relates to polymer supported or polymer bound metal complexes which exhibit activity as Fischer-Tropsch catalysts. Specifically, this invention relates to gas phase Fischer-Tropsch reactions wherein a resin metal complex catalyst is used in the conversion of synthesis gas to hydrocarbons.

BACKGROUND ART

There is a general belief by those skilled in the art of polymer supported catalysis that all types of polystyrene resins (macroreticular or gel) are inherently thermally unstable both in the presence or absence of oxygen. The upper temperature limit often cited for use of these catalyst-resin systems is quoted at approximately 150° C. See Sherrington "Polymer Supported Reactions in Organic Synthesis"; Chap.1 p.27; Wiley: New York, 1980; See also: International Workshop on Heterophase Attached Homogeneous Catalysis, Grenoble, France, 1977 (CNRS and NSF) and Chauvin et al, "Polymer Supported Catalysts" Prog. Polymer Sci., Vol. 5, p. 100, Pergamon Press, (1977). The present innovation is concerned with functionalized macroreticular polystyrene that has utility as a catalyst for vapor phase Fischer-Tropsch reactions at temperatures in excess of 200° C.

The use of a catalytic complex containing an anthranilic acid ligand for catalytic hydrogenation is disclosed in U.S. Pat. No. 3,755,194 to Avilov et al, issued Aug. 28, 1973. The Avilov patent relates to a homogeneous catalytic system for the hydrogenation of unsaturated compounds at room temperature and one atmosphere of hydrogen pressure. In this procedure a rhenium (I) complex of N-phenylanthranilic acid is employed. However, this procedure like other homogeneous catalytic systems has the disadvantage that it is difficult to separate the hydrogenation product from the catalyst itself with the result that the catalyst is a contaminant or an impurity in the final product.

Substituted phosphines have been used to chemically link a catalyst metal to a polymer support. Examples of this are found in Grubbs et al, "Polymer Preprints," American Chemical Society, Division Polymer Chemistry, 1972, Vol. 13, No. 2, pages 828-832 [Chem. Abs. Vol. 81, 6555d (1974)] and also Grubbs et al, "J. Macromol. Sci Chem.," 1973, Vol. 7, No. 5, Pages 1047-1063, [Chem. Abs. Vol. 78, 164622r (1973)].

U.S. Pat. No. 4,230,633 discloses polymer supported metal complexes wherein the ligand is a cycloalkadienyl radical with metals from Group VIII of the Periodic Table. This patent is concerned with the conversion of carbon monoxide and hydrogen to hydrocarbons in a liquid reaction medium.

U.S. Pat. No. 4,292,415 discloses a crosslinked polystyrene with cycloalkadienyl ligands and Group VIII metal carbonyls having utility as a Fischer-Tropsch catalyst in liquid phase reactions. This patent does not suggest the critical relationships that the present invention is concerned with, nor the specific ligands and vapor phase reactions.

Fischer-Tropsch catalysis by polystyrene supported cyclopentadienyldicarbonyl cobalt (CpCo(CO)$_2$) has been reported by Benner et al, (American Chemical Society Symposium Series 152 (1981) p. 165. The reaction was conducted in a medium pressure glass and stainless steel reactor. Benner et al suspended

in purified n-octane to swell the resin and allow access to catalyst sites in the interior of the beads; no detectable reaction took place if the solvent was excluded. This is in contrast to the present invention in which the reaction takes place in the vapor phase without the requirement that the polymer be swollen.

U.S. Pat. No. 4,323,698 discloses a weak base anion exchange resin which has been contacted with a solution of a coordination compound having at least two ligands connected to at least one central metal atom, to chemically bond the resin to the metal atom by replacement of at least one of the ligands of the coordination compound by a functional group of the weak base anion exchange resin. The complex can be used as a catalyst for hydrogenation, carbon monoxide insertion, polymerization, isomerization, vinyl ester exchange and ethylene oxidation reactions among others.

U.S. Pat. No. 4,144,191 discloses amine resins loaded with bimetallic clusters as novel hydroformylation catalysts. This patent is directed to the conversion of liquid olefins to alcohols in a one-step hydroformylation process which consists of contacting an olefin, such as 1-hexene in the liquid phase, with a gaseous mixture of carbon monoxide and hydrogen and the presence of a catalyst prepared by loading a bimetallic cluster onto an amine resin.

U.S. Pat. No. 4,238,358 discloses the use of anthranilic acid as a ligand for rhodium, palladium, platinum and ruthenium complexes. These catalysts are disclosed as reduction catalysts for liquid phase reactions, i.e. the hydrogenation of olefinic and aromatic hydrocarbons.

The prior art does not disclose or suggest the use of resin metal complex catalysts in vapor phase Fischer-Tropsch reactions. One skilled in this art would readily realize or assume that resins, particularly polystyrene resins would not hold up at the temperatures at which vapor phase Fischer-Tropsch reactions are conducted. See *Catalysis*, J. R. Anderson and M. Boudant, Eds. Chapter 4; Springer Verlag (1981). Specifically, the catalyst of the present invention operates in a temperature range from 175° to 275° C.

Synthesis gas is a mixture of carbon monoxide and hydrogen and can be produced by the gasification of coal with steam and oxygen. A description of conventional methods of coal gasification is provided in *McGraw-Hill Encyclopedia of Science & Technology*, 1977 Edition, Vol. 3, pages 248-249 (McGraw-Hill Book Company, New York).

Production of methane and higher hydrocarbons from coal by the Fischer-Tropsch reaction typically employs a group VIII catalyst (e.g. Fe, Co and Ni) at temperatures in the range of about 200°-350° C. and pressures in the range of about 2100-3500 kPa (300-500 psi).

While these processes are successful in making synthetic natural gas or oxygenated hydrocarbons, the operating conditions leave considerable room for improvement. The relatively severe operating conditions require high capital investment and power or energy consumption. In addition, the severe conditions present many operating problems. Accordingly, a catalyst which overcomes these disadvantages of the prior art processes is to be highly commended.

The present invention provides complexes useful as catalysts which enable Fischer-Tropsch synthesis to be achieved at mild operating temperatures and pressures.

DISCLOSURE OF THE INVENTION

There are three broad aspects to the present invention:

(1) novel polymer-metal complexes;
(2) a process for making the complexes, their activation, and
(3) the complexes as catalyst for Fischer-Tropsch reactions at relatively mild conditions.

Thus, there is disclosed novel polymer-supported metal complexes of the formula:

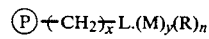

wherein
P represents a crosslinked macroreticular polystyrene resin which has a crosslink density of at least 5%;
x is 0 or 1;
L represents a ligand selected from the group consisting of bipyridyl, 2-aminopyridine, 2-amino phenol, 2-imino pyridine, sodium anthranilate, and potassium anthranilate;
y is an integer from 1 through 8;
when y equals 1, M represents a Group VIII metal from the Periodic Table and when y is from 2 through 8, M represents one or more metals selected from the group consisting of Group VIII metals from the Periodic Table, manganese, potassium and sodium with the proviso that at least one M is a Group VIII metal;
R represents a hydrogen carbonyl or a halogen radical; and
n represents an integer from 3 through 24.

Further, there is disclosed a heterogeneous catalyst for Fischer-Tropsch reactions conducted in the vapor phase at a temperature from 175° C. to 300° C., said catalyst comprising;

a ligand selected from the group consisting of, 2-amino phenol, 2-amino pyridine, bipyridyl and sodium or potassium anthranilate, which is complexed with a metal compound selected from the group consisting of $H_2FeRu_3(CO)_{13}$, $H_2FeOs_3(CO)_{13}$, $MnCo(CO)_9$, $RuCl_3$, $Co_4(CO)_{12}$, $H_4Ru_4(CO)_{12}$, $K_2Ru_6(CO)_{16}$, $Ru_3(CO)_{12}$, and $Fe_3(CO)_{12}$;

said ligand being chemically linked to a polymeric support, said polymeric support comprising from 0 to 20 weight percent chloromethylstyrene, 40 to 70 weight percent styrene and 20 to 40 weight percent divinylbenzene.

Some of the complexes of this invention are compositions based upon divinylbenzene crosslinked polystyrenes in which the divinylbenzene crosslinking is greater than 4 percent but less than 50 percent. This means that the divinylbenzene crosslinked polystyrenes are prepared with from 4-50% divinylbenzene based on monomer charge with the remainder being styrene and other monomers (i.e. chloromethylated vinyl benzene). Also, polystyrene may be halogenated and then further reacted. Thus, the polystyrene resins useful in this invention have pendant halomethyl functionally. The polymer may be a terpolymer in that other comonomers may be present in minor amounts.

The crosslinked chloromethylated polystyrene polymer is preferably macroporous or macroreticular in character (i.e. pore size of about 100 to 900 Å). Those skilled in the art are familiar with the manner of obtaining a macroporous polymer rather than a microporous polymer. See Sherrington supra.

EXPERIMENTAL

To these macroreticular divinylbenzene crosslinked chloromethylated polystyrene polymers are attached ligands. Conventionally, a ligand is a molecule, ion, or atom that is attached to the central atom of a coordination compound, a chelate, or other complex. For example, the ammonia molecules in $[Co(NH_3)_6]^{+++}$, and the chlorine atoms in $[PtCl_6]^{--}$ are ligands. Ligands are also called complexing agents, as for example EDTA, ammonia, etc. In the present invention the ligands are molecules that are attached to the polystyrene polymer and are capable of complexing with metal carbonyls or halides. Ligands such as anthranilic acid or other amines, i.e. 2-aminophenol, are anchored to the halomethylated polymer by known procedures such as stirring the polymer with excess anthranilic acid or other amines such as dipyridyl in a reaction medium such as ethyl ether, toluene, acetone, or dimethylformamide. As used herein, the term "dipyridyl" refers to the 2,2' isomer, which is also known as "bipyridyl".

The polymer is recovered and then washed with appropriate solvents such as ethanol. The polymer is then slurried in a reaction medium and there is added thereto the metal or metal cluster carbonyl or halide compound. Representative of the single metal carbonyls useful in the present invention are $Ru_3(CO)_{12}$, $Fe_3(CO)_{12}$, and $H_4Ru_4(CO)_{12}$. Mixed metal carbonyls such as $H_2FeRu_3(CO)_{13}$, $K_2Ru_6(CO)_{16}$, $H_2FeOs_3(CO)_{12}$, and $MnCo(CO)_9$ are also contemplated by the present invention. After stirring of this slurry for a suitable length of time, the polymer is recovered, e.g. by filtration, and washed and finally extracted to remove unreacted chemicals.

PREPARATION OF CATALYST FROM BOUND LIGAND AND METAL CARBONYLS

Anthranilic acid and 2-aminophenol were previously bound to polystyrene as described above. Both the polymer bound ligand (5 gm) and 0.73 gm of $Ru_3(CO)_{12}$ were weighed into a 250 ml 3 neck flask; then 100 ml of toluene was added. The flask was equipped with mechanical stirrer, thermometer, condenser, and nitrogen inlet/exit. The flask was flushed with nitrogen and heated to the 60° C. reaction temperature. During the overnight reaction, a nitrogen filled balloon maintained the reaction flask atmosphere. When the reaction was complete, the mixture was cooled and filtered through a polypropylene cloth to isolate the resin. The resin was washed with 500-1000 ml toluene and 200 ml hexane to remove most unreacted metal carbonyl. A 24 hour soxhlet extraction with hexane or 1:1 $THF/CH_3OH$ removed residual extractables. The extracted resin was vacuum dried at 50° C. for 3-4 hours. Synthesis of the metal complex was confirmed by elemental analysis, IR, weight gain, and color change.

Finally, the metal complex may be subjected to a treatment with a reducing agent, e.g. sodium borohydride, while suspended in a reaction medium. The reducing agent is used to selectively reduce the higher valence state of the metal to the lower catalytic state without affecting or reducing the anthranilic acid or amine ligand present in the catalytic complex.

Such reducing agents include, for example, sodium borohydride, metallic sodium (in ethanol), sodium hydride, and lithium aluminum hydride.

Polymeric supports in the form of beads, blocks, fibers, spheres, filaments, etc. may be used in the present invention. The use of polymers in the form of beads has been found to be advantageous since the ligand can be incorporated into such beads quite easily merely by stirring a mixture thereof in a suitable organic solvent or, if desired, with heating to a temperature as high as the reflux temperature of the system. The latter expedient may be employed for a better and faster incorporation of the ligand onto the beads. Polymeric beads having a size of about 1 to 10 mm can be suitably employed, although beads having a size as large as 2–5 cm. can also be used with advantage.

Particularly suitable, commercially available polymeric supports for use in the invention are polystyrene polymers (for example, Rohm and Haas XAD-4 Amberlite, or Dow Chemical XFS4022 resin), because of the ease of attaching different chemical groups. Also, chloromethylated polystyrene beads can be advantageously used as a polymeric support.

Other polymers having a reactive group can be provided with pendant functionality wherein, for example, anthranilic acid can be anchored to the polymer by a condensation reaction. Examples of such polymers include chlorinated polystyrene in which chlorine atoms can serve as reactive groups and copolymers of styrene with other copolymerizable monomers. In addition, they may be prepared as described in U.S. Pat. No. 2,597,437.

Further, in functional terms, the polymer support may additionally contain reactive functionalities such as sulfonate, methanesulfonate, tosylate, carboxylate, cyanomethyl and the like, which can be readily reacted so as to effect a condensation between the amino group of the ligand and the reactive groups of the polymeric chain. Thus, within this context, it is apparent that a wide variety of polymer supports can be used successfully in connection with the preparation of the heterogeneous catalytic systems of the invention.

Macroreticular resins can be synthesized by the polymerization of styrene, divinylbenzene and chloromethylstyrene using known procedures. The polymer crosslinks during the polymerization. Useful polymers contain 0–15 weight percent chloromethylstyrene, 40–70 weight percent styrene and 20–40 weight percent divinylbenzene.

Isoporous resins can be synthesized by polymerization of styrene and chloromethylstyrene. The polymer is crosslinked after polymerization with a $SnCl_4$ reaction. Chloromethylstyrene content can vary between 10 percent and 90 percent in the uncrosslinked polymer. For more information see, Regas and Papadoyannis, *Polymer Bulletin* 3, 279–284 (1980) and Peppas, Bussing and Slight, *Polymer Bulletin* 4, 193–198 (1981).

Macroporous and isoporous resins have different pore structures, swelling properties and physical properties because of the different crosslinking procedures. For this reason different catalytic properties might be expected.

The feedstock advantageously used by the catalysts of this invention is known as syngas or synthesis gas. Synthesis gas can be any of several gaseous mixtures used for synthesizing a wide range of compounds. Such mixtures result from reacting carbon-rich substances (ie. coal) with steam (steam reforming) or steam and oxygen (partial oxidation); they contain chiefly carbon monoxide and hydrogen, plus low percentages of carbon dioxide or nitrogen (less than 2.0%). The organic source materials may be natural gas, methane, naphtha, heavy petroleum oils, or coke (coal). The reactions are nickel-catalyzed steam-cracking (reforming) of methane or natural gas ($CH_4 + H_2O \rightarrow CO + 3H_2$); partial oxidation of methane, naphtha, or heavy oils; and especially in view of the petroleum shortage the water-gas reaction with coke ($C + H_2O \rightarrow CO + H_2$).

Synthesis gas with ratios of $H_2$ to $CO$ of from 1:1 to 2:1 have been found useful in the present invention. Other ratios would be appropriate, however, those skilled in this art will realize that changes in the ratio will affect the reaction in numerous ways.

REACTION SYSTEM USED FOR TESTS

Catalysts were utilized in a fixed bed reactor system. The reactor is a 1.4 cm ID × 38.1 cm (0.56 × 15 inch) 316 stainless steel tube. During catalyst tests the reactor contained about 10 cc of catalyst. Reactors were equipped with axial thermowells and a heating system capable of maintaining temperatures within 5° C. along the catalyst bed at 250° C. Each reactor was piped so that any of three gases could be passed through the bed.

1. Hydrogen (for catalyst reduction).
2. Helium (for purging).
3. Syngas ($H_2/CO = 2/1$).

The Fischer-Tropsch tests were conducted under the following conditions unless specified otherwise:

Synthesis gas molar ratio—2/1 $H_2/CO$
Pressure—1034 kPa (150 psig)
Temperature—250° C.
Gas hourly space velocity—200 $hr^{-1}$

CATALYST ACTIVATION

Activation procedures for polymer bound catalysts are the sodium borohydride process or vacuum with hydrogen reduction.

The sodium borohydride activation procedure consists of adding unactivated catalyst to absolute ethanol in a reaction flask. After adding a stirring bar, sodium borohydride was added in small batches. A 30 minute room temperature reaction was enough to complete the reduction. After isolation by filtration, the resin was washed with alcohol, petroleum ether and pentane. The pentane washed resin was charged to the reactor and dried with a helium stream.

Vacuum and hydrogen reduction activation consists of heating catalysts to a temperature between 225°–275° C. in a helium flow. The catalyst was then placed under vacuum for 1 hour. Thereafter, a 2 hour hydrogen flow reduced the evacuated catalyst. After activation the temperature was brought to 250° C. and the Fischer-Tropsch reaction was initiated by adding syngas.

The catalysts may be used without activation, wherein the catalyst is placed in the reactor, the temperature is raised to the reaction temperature and then syngas is introduced into the reactor. It has been unexpectedly discovered that non-activated catalyst will slowly activate in syngas with time until a steady state is achieved.

TEST DATA

Polymer bound amine ligated metal chloride and metal carbonyl complexes were tested for Fischer-Tropsch activity. Table I sets out the results of the screening test which utilized different metal complexes, different supporting resins or polymers and different ligands. The reaction conditions and reaction vessel were as previously described. All catalysts listed were *not* activated prior to testing unless otherwise noted. These catalysts were initially screened to determine whether or not they would exhibit any Fischer-Tropsch activity. More complete data on activity is presented infra.

All the active catalysts in Table I produced broad hydrocarbon product distributions in conjunction with very minor amounts of oxygenates such as methanol, ethanol and others. From Table I it is evident that benzyl iodide, double porphyrins and triphenyl phosphines are unacceptable ligands.

Catalyst Nos. 3, 7 and 9 after screening were subjected to an activation procedure which consisted of one hour under vacuum at 250° C. and then one hour under hydrogen at 250° C.

Tables II, III and IV set out CO conversion and light product selectivities for Catalyst Nos. 3, 7 and 9 respectively.

TABLE I

Polymer Bound Fischer-Tropsch Screening

| Catalyst # | Metal Cluster or Complex | Ligand | Resin ++ | Intended Metal Loading % by wt. | Fischer-Tropsch Activity |
|---|---|---|---|---|---|
| 1 | $H_2FeRu_3(CO)_{13}$ | Anthranilic Acid | A | 5 | Yes |
| 2 | $K_2Ru_6(CO)_{16}$ | Anthranilic Acid | A | 5 | Yes |
| 3 | $Ru_3(CO)_{12}$ | Anthranilic Acid | A | 5 | Yes |
| 4 | $RuCl_3$* | Potassium Anthranilate | A | 5 | Yes |
| 5 | $Ru_3(CO)_{12}$ | 2-amino phenol | A | 5 | Yes |
| 6 | $H_2FeOs_3(CO)_{13}$ | 2-amino pyridine | A | 5.5 | Yes |
| 7 | $Ru_3(CO)_{12}$ | 2-amino pyridine | A | 5 | Yes |
| 8 | $RuCl_3$* | 2-amino pyridine | A | 5 | Yes |
| 9 | $Ru_3(CO)_{12}$ | 2-imino pyridine | B | 5 | Yes |
| 10 | $HFeCo_3(CO)_{12}$ | Benzyl Iodide | C | 3 | No |
| 11 | $Fe_3(CO)_{12}$ | Dipyridyl | B | 3 | Yes |
| 12 | $H_2FeRu_3(CO)_{13}$ | Dipyridyl | B | 6 | Yes |
| 13 | $H_4Ru_4(CO)_{12}$ | Dipyridyl | B | 5 | Yes |
| 14 | $MnCo(CO)_9$ | Dipyridyl | B | 6 | Yes |
| 15 | $RhCl_3$* | Dipyridyl | B | 5 | Yes |
| 16 | $Ru_3(CO)_{12}$ | Dipyridyl | B | 5.2$^a$ | Yes |
| 17 | $RuCl_3$* | Dipyridyl | B | 5 | Yes |
| 18 | $IrCl_3$ | Double Porphyrin | A | N.A. | No |
| 19 | $RuCl_3$ | Double Porphyrin | A | 10 | No |
| 20 | $Co_4(CO)_{12}$ | Triphenyl Phosphine | B | 3 | No |
| 21 | $Fe_3(CO)_{12}$ | Triphenyl Phosphine | B | 3 | No |
| 22 | $Ru_3(CO)_{12}$ | Triphenyl Phosphine | B | 5 | No |

$^a$actually analyzed
*sodium borohydride activated prior to testing
++ Resin A is a 70/30 styrene/divinylbenzene macroreticular resin
Resin B is a Dow Chemical XFS4022 20% Divinylbenzene 80% styrene macroreticular resin
Resin C is vinyl benzyl chloride resin obtained from Ionac Inc.

TABLE II

CO Conversion and Light Product Selectivities for
$Ru_3(CO)_{12}$·Anthranilic Acid - Catalyst #3

| | Reaction Conditions | | | CO Conversion (%) | | | | | |
|---|---|---|---|---|---|---|---|---|---|
| Sample # | On-Stream Time (hr) | GHSV (hr$^{-1}$) | Temp. (°C.) | Total | To Hydrocarbon | $C_1$ | $C_2$ | $C_2^=$ | $C_3^+$ |
| 1 | 1.0 | 200 | 250 | 22.94 | 22.94 | 22.56 | 2.71 | 0.00 | 74.73 |
| 2 | 2.0 | 200 | 250 | 60.02 | 59.64 | 24.20 | 4.56 | 0.04 | 71.20 |
| 3 | 2.5 | 200 | 250 | 65.87 | 65.43 | 23.41 | 3.60 | 0.00 | 72.99 |
| 4 | 3.0 | 200 | 250 | 71.19 | 70.63 | 22.38 | 3.51 | 0.00 | 74.11 |
| 5 | 4.0 | 200 | 250 | 77.66 | 76.99 | 21.44 | 3.18 | 0.00 | 75.38 |
| 6 | 4.5 | 400 | 250 | 74.85 | 74.33 | 21.70 | 2.99 | 0.00 | 75.31 |
| 7 | 5.0 | 400 | 250 | 69.10 | 68.69 | 22.09 | 2.95 | 0.00 | 74.96 |
| | | | | OVERNIGHT SHUTDOWN: | | | | | |
| | | | CATALYST STORED UNDER HELIUM AT ROOM TEMPERATURE | | | | | | |
| 8 | 1.0 | 200 | 250 | 26.25 | 26.25 | 35.09 | 3.80 | 0.00 | 61.11 |
| 9 | 1.5 | 200 | 250 | 39.38 | 39.27 | 34.19 | 5.73 | 0.00 | 60.08 |
| 10 | 5.0 | 200 | 225 | 52.07 | 51.99 | 20.71 | 2.31 | 0.00 | 76.98 |
| 11 | 5.5 | 200 | 225 | 51.24 | 51.15 | 19.12 | 2.46 | 0.00 | 78.42 |

TABLE III

CO Conversion and Light Product Selectivities for
$Ru_3(CO)_{12}$.2-amino pyridine - Catalyst #7

| Sample # | Reaction Conditions | | | CO Conversion (%) | | Product Selectivity (%) | | | |
|---|---|---|---|---|---|---|---|---|---|
| | On-Stream Time (hr) | GHSV (hr$^{-1}$) | Temp. (°C.) | Total | To Hydrocarbon | $C_1$ | $C_2$ | $C_2$= | $C_3$+ |
| 1 | 1.5 | 200 | 250 | 54.27 | 53.56 | 30.19 | 3.98 | 0.00 | 65.83 |
| 2 | 3.0 | 200 | 250 | 63.37 | 62.31 | 29.51 | 3.61 | 0.00 | 66.88 |
| 3 | 3.5 | 200 | 250 | 62.60 | 61.64 | 29.96 | 3.52 | 0.00 | 66.52 |
| 4 | 4.0 | 400 | 250 | 42.27 | 41.79 | 34.07 | 3.80 | 0.00 | 62.13 |
| | OVERNIGHT SHUTDOWN: | | | | | | | | |
| | CATALYST STORED UNDER HELIUM AT ROOM TEMPERATURE | | | | | | | | |
| 5 | 1.0 | 200 | 250 | 44.55 | 44.21 | 48.61 | 4.65 | 0.00 | 46.74 |
| 6 | 1.75 | 200 | 250 | 45.49 | 45.16 | 46.42 | 4.71 | 0.00 | 48.87 |
| 7 | 3.0 | 200 | 225 | 27.19 | 27.05 | 34.14 | 3.22 | 0.00 | 62.64 |
| 8 | 3.33 | 200 | 225 | 23.38 | 23.32 | 30.52 | 2.77 | 0.00 | 66.71 |
| 9 | 5.66 | 200 | 250 | 40.87 | 40.58 | 43.50 | 4.11 | 0.00 | 52.39 |

TABLE IV

CO Conversion and Light Product Selectivities for
$Ru_3(CO)_{12}$.2-imino pyridine - Catalyst #9

| Sample # | Reaction Conditions | | | CO Conversion (%) | | Product Selectivity (%) | | | |
|---|---|---|---|---|---|---|---|---|---|
| | On-Stream Time (hr) | GHSV (hr$^{-1}$) | Temp. (°C.) | Total | To Hydrocarbon | $C_1$ | $C_2$ | $C_2$= | $C_3$+ |
| 1 | 1.25 | 200 | 250 | 5.88 | 5.88 | 30.07 | 0.00 | 0.00 | 69.93 |
| 2 | 2.33 | 200 | 250 | 5.32 | 5.32 | 27.73 | 0.00 | 0.00 | 72.27 |
| 3 | 4.50 | 200 | 250 | 5.40 | 5.40 | 24.68 | 0.00 | 0.00 | 75.32 |
| 4 | 6.00 | 200 | 275 | 9.14 | 9.15 | 52.28 | 0.00 | 0.00 | 47.72 |

The data contained in Tables II, III, and IV demonstrates that catalysts according to the present invention have acceptable Fischer-Tropsch activity. To further demonstrate the activity of the catalysts of the instant invention 11 active catalysts from Table I were activated and then subjected to extensive testing for Fischer-Tropsch activity. This data is set out in the following Tables V through XVI.

TABLE V

CO Conversion and Light Product Selectivities for
$H_2FeRu_3(CO)_{13}$.Anthranilic Acid - Catalyst #1
Activated by three hours under vacuum at 250° C. and one hour under $H_2$ at 250° C.

| Sample # | Reaction Conditions | | | CO Conversion (%) | | Product Selectivity (%) | | | |
|---|---|---|---|---|---|---|---|---|---|
| | On-Stream Time (hr) | GHSV (hr$^{-1}$) | Temp. (°C.) | Total | To Hydrocarbon | $C_1$ | $C_2$ | $C_2$= | $C_3$+ |
| 1 | 1.00 | 200 | 250 | 31.54 | 31.44 | 22.15 | 4.05 | 0.00 | 73.80 |
| 2 | 17.50 | 200 | 250 | 48.97 | 58.55 | 22.12 | 2.84 | 0.00 | 75.04 |
| 3 | 25.00 | 200 | 250 | 53.72 | 53.20 | 23.53 | 3.10 | 0.00 | 73.37 |
| 4 | 41.00 | 200 | 250 | 50.47 | 49.76 | 25.88 | 3.39 | 0.00 | 70.73 |
| 5 | 47.00 | 200 | 250 | 49.82 | 49.06 | 25.67 | 3.39 | 0.00 | 70.94 |
| 6 | 114.75 | 200 | 250 | 44.33 | 43.25 | 26.91 | 3.85 | 0.00 | 69.24 |
| 7 | 120.50 | 200 | 250 | 44.49 | 43.40 | 26.55 | 3.69 | 0.00 | 69.76 |

TABLE VI

CO Conversion and Light Product Selectivities for
$K_2Ru_6(CO)_{16}$.Anthranilic Acid at - Catalyst #2
Activated one hour under vacuum at 250° C. and one hour under $H_2$ at 250° C.

| Sample # | Reaction Conditions | | | CO Conversion (%) | | Product Selectivity (%) | | | |
|---|---|---|---|---|---|---|---|---|---|
| | On-Stream Time (hr) | GHSV (hr$^{-1}$) | Temp. (°C.) | Total | To Hydrocarbon | $C_1$ | $C_2$ | $C_2$= | $C_3$+ |
| 1 | 2.00 | 200 | 250 | 42.83 | 41.98 | 19.22 | 2.87 | 0.00 | 77.91 |
| 2 | 4.50 | 200 | 250 | 45.54 | 44.71 | 21.01 | 2.77 | 0.00 | 76.22 |
| 3 | 23.00 | 200 | 250 | 34.63 | 22.74 | 22.74 | 3.26 | 0.00 | 74.00 |
| 4 | 24.00 | 200 | 250 | 37.20 | 37.20 | 20.84 | 2.56 | 0.00 | 76.60 |
| 5 | 27.00 | 200 | 250 | 35.53 | 35.53 | 22.60 | 2.65 | 0.00 | 74.75 |
| 6 | 47.25 | 200 | 250 | 33.33 | 33.33 | 22.94 | 2.63 | 0.00 | 74.43 |
| 7 | 53.00 | 200 | 275[a] | 51.06 | 50.73 | 37.55 | 4.77 | 0.00 | 57.68 |
| 8 | 70.50 | 200 | 275[a] | 59.97 | 59.45 | 42.01 | 5.54 | 0.00 | 52.45 |
| 9 | 75.00 | 200 | 275[a] | 59.68 | 59.18 | 42.05 | 5.53 | 0.00 | 52.42 |

[a]Pressure Rose to 180 psig

TABLE VII

CO Conversion and Light Product Selectivities for
RuCl₃.Potassium Anthranilate - Catalyst #4
Activated one hour under vacuum at 250° C. and one hour under H₂ at 250° C.

| | Reaction Conditions | | | CO Conversion (%) | | | | | |
|---|---|---|---|---|---|---|---|---|---|
| | On-Stream | GHSV | Temp. | | To | Product Selectivity (%) | | | |
| Sample # | Time (hr) | (hr$^{-1}$) | (°C.) | Total | Hydrocarbon | $C_1$ | $C_2$ | $C_2^=$ | $C_3^+$ |
| 1 | 2.80 | 150 | 250 | 71.15 | 69.66 | 17.59 | 2.81 | 0.00 | 79.60 |
| 2 | 4.08 | 150 | 250 | 76.90 | 75.26 | 16.51 | 2.59 | 0.00 | 80.90 |
| 3 | 23.25 | 400 | 250 | 42.08 | 42.01 | 17.84 | 2.04 | 0.00 | 80.12 |
| 4 | 27.50 | 400 | 250 | 40.87 | 40.78 | 17.94 | 2.17 | 0.00 | 79.89 |
| 5 | 45.50 | 400 | 250 | 40.08 | 39.98 | 17.37 | 2.17 | 0.00 | 80.46 |
| 6 | 116.75 | 400 | 250 | 40.12 | 39.98 | 14.69 | 2.00 | 0.00 | 83.30 |

TABLE VIII

CO Conversion and Light Product Selectivities for
Ru₃(CO)₁₂.2-amino phenol - Catalyst #5
Activated one hour under vacuum at 250° C. and one hour under H₂ at 250° C.

| | Reaction Conditions | | | CO Conversion (%) | | | | | |
|---|---|---|---|---|---|---|---|---|---|
| | On-Stream | GHSV | Temp. | | To | Product Selectivity (%) | | | |
| Sample # | Time (hr) | (hr$^{-1}$) | (°C.) | Total | Hydrocarbon | $C_1$ | $C_2$ | $C_2^=$ | $C_3^+$ |
| 1 | 0.75 | 200 | 250 | 16.37 | 16.37 | 43.37 | 5.35 | 0.00 | 51.28 |
| 2 | 2.00 | 200 | 250 | 47.99 | 47.99 | 40.41 | 4.91 | 0.00 | 54.68 |
| 3 | 3.00 | 200 | 250 | 39.05 | 39.05 | 41.05 | 4.66 | 0.00 | 54.29 |
| 4 | 4.00 | 200 | 250 | 33.94 | 33.94 | 41.73 | 4.32 | 0.00 | 53.95 |
| 5 | 5.00 | 200 | 250 | 37.57 | 37.47 | 43.00 | 4.32 | 0.00 | 52.68 |
| 6 | 20.72 | 200 | 250 | 37.97 | 37.97 | 47.32 | 3.88 | 0.00 | 48.80 |
| 7 | 24.72 | 200 | 250 | 38.10 | 38.10 | 47.15 | 4.07 | 0.00 | 48.79 |
| 8 | 27.00 | 200 | 275 | 56.21 | 55.92 | 71.23 | 6.09 | 0.00 | 22.68 |
| 9 | 29.00 | 400 | 275 | 49.07 | 48.96 | 75.47 | 5.76 | 0.00 | 18.76 |
| 10 | 45.50 | 400 | 275 | 44.45 | 44.38 | 74.75 | 5.42 | 0.00 | 19.83 |
| 11 | 46.50 | 400 | 275 | 44.78 | 44.70 | 73.95 | 5.33 | 0.00 | 20.72 |
| 12 | 50.00 | 400 | 250 | 28.67 | 28.67 | 45.17 | 3.89 | 0.00 | 50.94 |
| 13 | 51.00 | 400 | 250 | 26.40 | 26.40 | 49.62 | 4.30 | 0.00 | 46.08 |

TABLE IX

CO Conversion and Light Product Selectivities for
H₂FeOs₃(CO)₁₃.2-amino pyridine - Catalyst #6
Activated one hour under vacuum and 1.25 hours under H₂ at 250° C.

| | Reaction Conditions | | | CO Conversion (%) | | | | | |
|---|---|---|---|---|---|---|---|---|---|
| | On-Stream | GHSV | Temp. | | To | Product Selectivity (%) | | | |
| Sample # | Time (hr) | (hr$^{-1}$) | (°C.) | Total | Hydrocarbon | $C_1$ | $C_2$ | $C_2^=$ | $C_3^+$ |
| 1 | 1.00 | 200 | 250 | 16.82 | 16.82 | 17.01 | 6.19 | 1.41 | 75.39 |
| 2 | 2.00 | 200 | 250 | 7.88 | 7.77 | 31.05 | 10.82 | 2.68 | 55.45 |
| 3 | 19.00 | 200 | 250 | 13.42 | 13.42 | 23.54 | 6.13 | 2.13 | 68.20 |
| 4 | 27.50 | 200 | 250 | 13.22 | 13.22 | 25.14 | 5.32 | 2.97 | 66.57 |
| 5 | 44.50 | 200 | 250 | 14.66 | 14.53 | 26.82 | 5.27 | 4.19 | 63.72 |
| 6 | 48.25 | 200 | 275 | 32.18 | 31.18 | 32.00 | 7.16 | 2.92 | 57.92 |
| 7 | 117.50 | 200 | 275 | 40.15 | 33.74 | 43.71 | 10.64 | 0.69 | 44.96 |
| 8 | 123.00 | 200 | 275 | 42.27 | 35.37 | 43.48 | 10.75 | 0.71 | 45.06 |

TABLE X

CO Conversion and Light Product Selectivities for
RuCl₃.2-amino pyridine - Catalyst #8
Activated one hour under vacuum and one hour under H₂ at 250° C.

| | Reaction Conditions | | | CO Conversion (%) | | | | | |
|---|---|---|---|---|---|---|---|---|---|
| | On-Stream | GHSV | Temp. | | To | Product Selectivity (%) | | | |
| Sample # | Time (hr) | (hr$^{-1}$) | (°C.) | Total | Hydrocarbon | $C_1$ | $C_2$ | $C_2^=$ | $C_3^+$ |
| 1 | 0.72 | 200 | 250 | 20.29 | 20.05 | 18.79 | 2.56 | 0.00 | 78.65 |
| 2 | 1.67 | 200 | 250 | 28.30 | 27.82 | 19.74 | 2.32 | 0.00 | 77.94 |
| 3 | 2.66 | 200 | 250 | 26.54 | 26.22 | 20.16 | 1.99 | 0.00 | 77.85 |
| 4 | 19.70 | 200 | 250 | 15.81 | 15.81 | 23.07 | 0.00$^a$ | 0.00 | 76.93 |
| 5 | 23.95 | 200 | 250 | 16.48 | 16.48 | 21.63 | 2.54 | 0.00 | 75.83 |
| 6 | 43.95 | 200 | 250 | 16.07 | 16.07 | 20.44 | 1.88 | 0.00 | 77.68 |
| 7 | 45.45 | 200 | 275 | 30.54 | 30.41 | 41.55 | 3.63 | 0.00 | 54.82 |
| 8 | 47.45 | 200 | 275 | 33.40 | 33.28 | 41.29 | 4.52 | 0.00 | 54.19 |
| 9 | 48.45 | 200 | 275 | 33.07 | 32.95 | 42.63 | 4.76 | 0.00 | 52.61 |

$^a$Trace ethane formed missed by integrator

TABLE XI

CO Conversion and Light Product Selectivities for
$H_2FeRu_3(CO)_{12}$·Dipyridyl - Catalyst #12
Activated one hour under vacuum and one hour under $H_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | $C_1$ | $C_2$ | $C_2^=$ | $C_3^+$ |
| 1 | 2.25 | 200 | 250 | 18.08 | 16.67 | 27.21 | 4.46 | 0.00 | 68.33 |
| 2 | 4.00 | 200 | 250 | 20.93 | 19.98 | 26.95 | 3.96 | 0.00 | 69.09 |
| 3 | 5.00 | 200 | 250 | 23.66 | 22.73 | 19.83 | 4.47 | 0.00 | 75.70 |
| 4 | 21.17 | 200 | 250 | 20.93 | 20.59 | 24.19 | 2.75 | 0.00 | 73.06 |
| 5 | 26.50 | 200 | 250 | 18.54 | 18.17 | 28.19 | 3.40 | 0.00 | 68.41 |
| 6 | 45.50 | 200 | 250 | 18.06 | 17.82 | 28.81 | 3.77 | 0.00 | 67.42 |
| 7 | 51.00 | 200 | 250 | 18.26 | 18.01 | 28.17 | 3.37 | 0.00 | 68.36 |
| 8 | 117.50 | 200 | 250 | 17.82 | 17.71 | 29.25 | 2.94 | 0.00 | 67.81 |
| 9 | 122.50 | 200 | 275 | 49.66 | 48.28 | 35.78 | 5.22 | 0.00 | 59.00 |
| 10 | 125.00 | 200 | 275 | 51.03 | 49.57 | 35.86 | 4.77 | 0.00 | 59.37 |
| 11 | 144.00 | 200 | 275 | 51.92 | 50.62 | 33.83 | 4.60 | 0.00 | 61.57 |
| 12[a] | 149.00 | 200 | 250 | 18.58 | 18.31 | 29.63 | 4.74 | 0.00 | 65.63 |
| 13[a] | 165.50 | 200 | 250 | 39.12 | 38.89 | 22.41 | 2.26 | 0.00 | 75.33 |
| 14[a] | 167.50 | 200 | 250 | 38.70 | 38.47 | 22.47 | 2.30 | 0.00 | 75.23 |
| 15[b] | 171.50 | 200 | 250 | 15.48 | 15.41 | 26.37 | 3.12 | 0.00 | 70.49 |
| 16[b] | 189.50 | 200 | 250 | 16.06 | 16.00 | 26.15 | 2.68 | 0.00 | 71.17 |

[a]350 psig (2413 kPa)
[b]80 psig (552 kPa)

TABLE XII

CO Conversion and Light Product Selectivities for
$H_4Ru_4(CO)_{12}$·Dipyridyl - Catalyst #13
Activated one hour under vacuum and one hour under $H_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | $C_1$ | $C_2$ | $C_2^=$ | $C_3^+$ |
| 1 | 1.50 | 200 | 250 | 22.19 | 22.19 | 52.61 | 5.59 | 0.00 | 41.80 |
| 2 | 3.50 | 200 | 250 | 22.64 | 22.64 | 50.10 | 5.31 | 0.00 | 44.59 |
| 3 | 20.50 | 200 | 250 | 24.05 | 25.05 | 45.41 | 4.18 | 0.00 | 50.41 |
| 4 | 28.00 | 200 | 250 | 23.58 | 23.58 | 45.63 | 4.39 | 0.00 | 49.98 |
| 5 | 45.50 | 200 | 250 | 22.64 | 22.64 | 46.30 | 4.34 | 0.00 | 49.36 |
| 6 | 51.00 | 200 | 250 | 23.04 | 23.04 | 44.81 | 4.41 | 0.00 | 50.78 |
| 7 | 69.50 | 200 | 250 | 23.43 | 23.43 | 43.99 | 3.92 | 0.00 | 52.09 |
| 8 | 73.50 | 200 | 275 | 32.26 | 32.26 | 67.45 | 5.39 | 0.00 | 27.16 |

TABLE XIII

CO Conversion and Light Product Selectivities for
$MnCo(CO)_9$·Dipyridyl - Catalyst #14
Activated one hour under vacuum and one hour under $H_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | $C_1$ | $C_2$ | $C_2^=$ | $C_3^+$ |
| 1 | 3.00 | 200 | 250 | 8.82 | 8.82 | 10.32 | 0.00[a] | 0.00[a] | 89.68 |
| 2 | 4.50 | 200 | 250 | 9.91 | 9.91 | 10.71 | 0.00[a] | 0.00[a] | 89.29 |
| 3 | 21.50 | 200 | 250 | 8.89 | 8.89 | 7.03 | 0.98 | 9.17[b] | 82.81 |
| 4 | 24.50 | 200 | 275 | 26.57 | 25.53 | 12.01 | 3.97 | 2.54 | 81.48 |
| 5 | 28.50 | 200 | 275 | 27.65 | 26.64 | 11.72 | 4.09 | 1.97 | 82.22 |
| 6 | 46.50 | 200 | 275 | 21.78 | 21.02 | 13.09 | 4.56 | 1.56 | 80.79 |
| 7 | 52.50 | 200 | 275 | 20.12 | 19.52 | 16.18 | 4.84 | 1.33 | 77.65 |
| 8 | 70.50 | 200 | 275 | 16.68 | 16.27 | 17.58 | 4.05 | 0.83 | 77.54 |

[a]Trace peaks present could not be distinguished from noise by integrator
[b]Overestimated due to noise

TABLE XIV

CO Conversion and Light Product Selectivities for
$RuCl_3$·Dipyridyl - Catalyst #15
Activated one hour under vacuum and one hour under $H_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | $C_1$ | $C_2$ | $C_2^=$ | $C_3^+$ |
| 1 | 1.00 | 200 | 250 | 7.24 | 7.24 | 24.67 | 2.95 | 0.00 | 72.38 |
| 2 | 4.00 | 200 | 250 | 5.92 | 5.92 | 31.94 | 0.00 | 0.00 | 68.06 |
| 3 | 20.25 | 200 | 250 | 3.42 | 3.42 | 26.69 | 0.00 | 0.00 | 73.31 |
| 4 | 22.50 | 200 | 275 | 6.45 | 6.45 | 50.24 | 0.00 | 0.00 | 49.76 |
| 5 | 26.50 | 200 | 275 | 6.85 | 6.85 | 47.24 | 6.59 | 0.00 | 46.17 |
| 6 | 28.00 | 200 | 275 | 6.72 | 6.72 | 46.89 | 6.37 | 0.00 | 46.74 |

TABLE XIV-continued

CO Conversion and Light Product Selectivities for
RuCl$_3$.Dipyridyl - Catalyst #15
Activated one hour under vacuum and one hour under H$_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | C$_1$ | C$_2$ | C$_2$= | C$_3$+ |
| 7 | 93.00 | 200 | 275 | 5.59 | 5.59 | 41.96 | 11.07 | 0.00 | 46.97 |
| 8$^a$ | 98.00 | 200 | 275 | 5.30 | 5.30 | 41.19 | 9.22 | 0.00 | 49.59 |
| 9$^a$ | 100.00 | 200 | 275 | 6.67 | 6.67 | 49.04 | 7.68 | 0.00 | 43.28 |

$^a$Reactor Pressure = 250 psig (1724 kPa)

TABLE XV

CO Conversion and Light Product Selectivities for
Ru$_3$(CO)$_{12}$.Dipyridyl - Catalyst #16
Activated one hour under vacuum and 1.5 hours under H$_2$ at 250° C.

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | C$_1$ | C$_2$ | C$_2$= | C$_3$+ |
| 1 | 3.33 | 200 | 250 | 38.95 | 38.95 | 42.73 | 4.97 | 0.00 | 52.30 |
| 2 | 6.67 | 200 | 250 | 39.36 | 39.36 | 40.09 | 4.64 | 0.00 | 55.27 |
| 3 | 24.50 | 200 | 250 | 38.77 | 38.77 | 39.04 | 4.33 | 0.00 | 56.63 |
| 4 | 28.00 | 200 | 275 | 50.10 | 50.02 | 56.24 | 6.25 | 0.00 | 37.51 |
| 5 | 30.33 | 200 | 275 | 53.38 | 53.37 | 58.75 | 6.66 | 0.00 | 34.57 |
| 6 | 118.91 | 400 | 275 | 56.73 | 56.67 | 61.87 | 6.07 | 0.00 | 32.06 |
| 7 | 120.64 | 400 | 275 | 56.90 | 56.86 | 61.41 | 6.03 | 0.00 | 32.56 |
| 8 | 124.39 | 400 | 250 | 47.78 | 47.78 | 32.78 | 3.49 | 0.00 | 63.73 |
| 9 | 125.74 | 400 | 250 | 50.51 | 50.51 | 31.46 | 3.29 | 0.00 | 65.25 |
| 10 | 142.92 | 400 | 250 | 56.53 | 56.53 | 28.30 | 2.96 | 0.00 | 68.74 |
| 11 | 149.85 | 400 | 250 | 57.05 | 57.05 | 28.00 | 2.88 | 0.00 | 69.12 |
| 12 | 172.93 | 400 | 225 | 43.84 | 43.84 | 12.38 | 0.74 | 0.00 | 86.88 |
| 13 | 191.13 | 400 | 225 | 50.23 | 50.23 | 11.24 | 0.72 | 0.00 | 88.04 |
| 14 | 193.35 | 400 | 225 | 50.29 | 50.29 | 11.27 | 0.69 | 0.00 | 88.04 |
| 15 | 196.35 | 400 | 175 | 13.58 | 13.58 | 1.32 | 0.00 | 0.00 | 98.68 |
| 16 | 214.93 | 400 | 175 | 11.60 | 11.60 | 1.63 | 0.00 | 0.00 | 98.37 |

TABLE XVI

CO Conversion and Light Product Selectivities for
RuCl$_3$.Dipyridyl - Catalyst #17
No activation other than that noted on Table I

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | C$_1$ | C$_2$ | C$_2$= | C$_3$+ |
| 1 | 2.75 | 200 | 250 | 6.04 | 6.04 | 20.95 | 0.00 | 0.00 | 79.05 |
| 2 | 6.83 | 200 | 250 | 6.11 | 6.11 | 20.45 | 0.00 | 0.00 | 79.55 |
| 3 | 27.16 | 200 | 250 | 5.99 | 5.99 | 18.35 | 0.00 | 0.00 | 81.65 |
| 4 | 29.33 | 200 | 275 | 12.73 | 12.73 | 39.62 | 5.41 | 0.00 | 54.97 |
| 5 | 120.25 | 200 | 275 | 20.11 | 20.11 | 39.23 | 3.96 | 0.00 | 56.80 |
| 6 | 144.21 | 200 | 275 | 21.67 | 21.67 | 37.14 | 3.84 | 0.00 | 59.02 |
| 7 | 168.23 | 200 | 275 | 22.55 | 22.55 | 37.62 | 4.05 | 0.00 | 58.33 |
| | HYDROGEN TREATMENT: 250° C., 50 PSIG, 40 SCCM*, ONE HOUR | | | | | | | | |
| 8 | 17.75 | 200 | 250 | 19.69 | 19.69 | 18.41 | 2.12 | 0.00 | 79.73 |
| 9 | 20.02 | 200 | 250 | 19.64 | 19.64 | 18.22 | 0.00$^a$ | 0.00 | 81.78 |
| 10 | 24.27 | 200 | 275 | 28.98 | 28.98 | 42.17 | 4.64 | 0.00 | 53.19 |
| 11 | 41.60 | 200 | 275 | 29.55 | 29.46 | 40.93 | 4.25 | 0.00 | 54.82 |

$^a$Trace Ethane formed, missed by integrator
*Standard Cubic Centimeters per Minute

TABLE XVII

CO Conversion and Light Product Selectivities for
Ru on Al$_2$O$_3$ - Comparative

| | Reaction Conditions | | | CO Conversion (%) | | Product Selectivity (%) | | | |
|---|---|---|---|---|---|---|---|---|---|
| Sample # | On-Stream Time (hr) | GHSV (hr$^{-1}$) | Temp. (°C.) | Total | To Hydrocarbon | C$_1$ | C$_2$ | C$_2$= | C$_3$+ |
| 1 | 0.50 | 200 | 250 | 54.80 | 47.07 | 70.94 | 3.14 | 0.00 | 25.92 |
| 2 | 1.00 | 200 | 250 | 58.61 | 50.71 | 66.41 | 3.40 | 0.00 | 30.19 |
| 3 | 18.50 | 200 | 250 | 95.39 | 91.58 | 7.75 | 1.71 | 0.00 | 90.54 |
| 4 | 21.00 | 400 | 250 | 87.87 | 85.73 | 9.22 | 1.86 | 0.00 | 88.92 |
| 5 | 24.50 | 400 | 225 | 70.65 | 69.85 | 8.75 | 1.55 | 0.15 | 89.55 |
| 6 | 42.00 | 400 | 225 | 57.97 | 57.86 | 8.60 | 0.86 | 0.00 | 90.54 |
| 7 | 45.00 | 400 | 225 | 53.25 | 53.23 | 9.70 | 1.03 | 0.00 | 89.27 |

TABLE XVII-continued

CO Conversion and Light Product Selectivities for
Ru on $Al_2O_3$ - Comparative

| Sample # | Reaction Conditions | | | CO Conversion (%) | | Product Selectivity (%) | | | |
|---|---|---|---|---|---|---|---|---|---|
| | On-Stream Time (hr) | GHSV $(hr^{-1})$ | Temp. (°C.) | Total | To Hydrocarbon | $C_1$ | $C_2$ | $C_2^=$ | $C_3^+$ |
| 8 | 48.25 | 400 | 225 | 53.28 | 53.27 | 9.63 | 0.92 | 0.00 | 89.45 |

For a comparison with a conventional Fischer-Tropsch catalyst, Ru on $Al_2O_3$ was prepared by a conventional literature procedure and tested in the reactor system. From Table XVII it can be seen that the conventional $Ru/Al_2O_3$ catalyst was more active at 250° C. than any polymer bound catalyst. However, at 225° C. (53% conversion), the $Ru_3(CO)_{12}$ catalyst #16 was nearly as active ($\approx$50% conversion). Thus polymer bound catalysts can achieve acceptable Fischer-Tropsch activity at lower temperatures, thus saving energy. Tables XVIII through XXVI set out product selectivities for selected catalysts at different times during a run and at different GHSV, temperatures and pressures. It is evident from the data that Catalyst #14 ($MnCo(CO)_9$-Dipyridyl) and Catalyst #6 ($H_2FeOs_3$-$(CO)_{13}$-2Amino Phenol) produced a substantial amount of olefins.

TABLE XVIII $C_1$-$C_9+$ Product Selectivities and Olefin Fractions for
$Ru_3(CO)_{12}$.Anthranilic Acid at 250° C., 1034 kPa (150 psig)
200 $hr^{-1}$ - Catalyst #3

| | Carbon Number | | | | | | |
|---|---|---|---|---|---|---|---|
| | 1 | 2 | 3 | 4 | 5 | 6-8 | 9+ |
| Carbon % | 24.20 | 4.56 | 6.33 | 6.09 | 3.84 | 0.67 | 54.31 |
| Olefin % | — | 0.00 | 10.18 | 24.72 | 12.50 | NA | NA |

TABLE XIX $C_1$-$C_9+$ Product Selectivities and Olefin Fractions for
$H_2FeRu_3(CO)_{13}$.Anthranilic Acid at 250° C.
1034 kPa (150 psig), 200 $hr^{-1}$,
After 23 hours on stream - Catalyst #1

| | Carbon Number | | | | | | |
|---|---|---|---|---|---|---|---|
| | 1 | 2 | 3 | 4 | 5 | 6-8 | 9+ |
| Carbon % | 22.7 | 3.05 | 3.08 | 3.08 | 2.12 | 0.59 | 65.38 |
| Olefin % | — | 17.56 | 36.02 | 38.48 | 37.39 | NA | NA |

TABLE XX $C_1$-$C_9+$ Product Selectivities and Olefin Fractions for
$K_2Ru_6(CO)_{16}$.Anthranilic Acid at 250° C. 1034 kPa (150 psig)
200 $hr^{-1}$ After 25 hours on stream - Catalyst #2

| | Carbon Number | | | | | | |
|---|---|---|---|---|---|---|---|
| | 1 | 2 | 3 | 4 | 5 | 6-8 | 9+ |
| Carbon % | 20.84 | 2.56 | 1.71 | 2.04 | 1.91 | 0.96 | 69.98 |
| Olefin % | — | 0.00 | 40.38 | 43.94 | 47.61 | NA | NA |

TABLE XXI $C_1$-$C_9+$ Product Selectivities and Olefin Fractions for
$H_2FeOs_3(CO)_{13}$.2Aminopyridine
at 1034 kPa (150 psig) - Catalyst #6

| | Carbon Number | | | | | | |
|---|---|---|---|---|---|---|---|
| | 1 | 2 | 3 | 4 | 5 | 6-8 | 9+ |
| Carbon % | 26.82 | 9.46 | 13.54 | 8.32 | 3.05 | 0.42 | 38.39 |
| Olefin % | — | 51.47 | 63.05 | 58.85 | 40.30 | NA | NA |

TABLE XXII $C_1$-$C_9+$ Product Selectivities and Olefin Fractions for
$H_4Ru_4(CO)_{12}$.Dipyridyl at 250° C. - Catalyst #13

| | Carbon Number | | | | | | |
|---|---|---|---|---|---|---|---|
| | 1 | 2 | 3 | 4 | 5 | 6-8 | 9+ |
| Carbon % | 43.99 | 3.92 | 4.56 | 4.08 | 3.16 | 2.96 | 37.33 |
| Olefin % | — | 0.00 | 12.63 | 24.65 | 13.53 | NA | NA |

TABLE XXIII $C_1$-$C_9+$ Product Selectivities and Olefin Fractions for
$MnCo(CO)_9$.Dipyridyl at 275° C. - Catalyst #14

| | Carbon Number | | | | | | |
|---|---|---|---|---|---|---|---|
| | 1 | 2 | 3 | 4 | 5 | 6-8 | 9+ |
| Carbon % | 11.72 | 6.06 | 7.33 | 4.87 | 3.28 | 1.48 | 65.26 |
| Olefin % | — | 35.12 | 82.12 | 78.56 | 77.17 | NA | NA |

TABLE XXIV $C_1$-$C_9+$ Product Selectivities and Olefin Fractions for
$RuCl_3$.Dipyridyl at 275° C. - Catalyst #15

| | Carbon Number | | | | | |
|---|---|---|---|---|---|---|
| | 1 | 2 | 3 | 4 | 5 | 6-8 9+ |
| Carbon % | 37.62 | 4.05 | 4.07 | 3.47 | 3.11 | [52.68][a] |
| Olefin % | — | 25.88 | 47.75 | 56.31 | 60.07 | NA |

[a]$C_{6-8}$ and $C_{9+}$ peaks combined

TABLE XXV $C_1$-$C_9+$ Product Selectivities and Olefin Fractions for
$Ru_3(CO)_{12}$.Dipyridyl at 250° C. - Catalyst #16

| | Carbon Number | | | | | | |
|---|---|---|---|---|---|---|---|
| | 1 | 2 | 3 | 4 | 5 | 6-8 | 9+ |
| Carbon % | 28.00 | 2.88 | 5.13 | 4.91 | 2.83 | 2.54 | 53.71 |
| Olefin % | — | 0.00 | 38.02 | 44.82 | 24.02 | NA | NA |

TABLE XXVI $C_1$-$C_9+$ Product Selectivities and Olefin Fractions for
$RuCl_3$.Dipyridyl at 225° C. (25 hours on stream) Catalyst #17

| | Carbon Number | | | | | | |
|---|---|---|---|---|---|---|---|
| | 1 | 2 | 3 | 4 | 5 | 6-8 | 9+ |
| Carbon % | 9.63 | 1.16 | 9.65 | 11.08 | 5.45 | 1.28 | 61.75 |
| Olefin % | — | 20.07 | 68.37 | 63.90 | 59.20 | NA | NA |

The discovery of the instant invention can be more fully appreciated when one realizes that modification of the polymer bound catalyst can be made to achieve certain desired results from the vapor phase Fischer-Tropsch reaction. Tables XXVII and XXVIII demonstrate that the metal affects selectivity.

TABLE XXVII

Methane Selectivity Comparison for
Three Ru.Dipyridyl Catalysts at 250° C.

| # | Catalyst | On-Stream Time (hr) | Methane Selectivity (%) |
|---|---|---|---|
| 17 | $RuCl_3$— | 27.16 | 18.35 |
| 16 | $Ru_3(CO)_{12}$— | 24.50 | 39.04 |

TABLE XXVII-continued

Methane Selectivity Comparison for
Three Ru.Dipyridyl Catalysts at 250° C.

| # | Catalyst | On-Stream Time (hr) | Methane Selectivity (%) |
|---|---|---|---|
| 13 | H₄Ru₄(CO)₁₂— | 28.00 | 45.63 |

TABLE XXVIII

C₂-C₅ Olefin Fraction Comparison for
Five Dipyridyl Catalysts

| # | Catalyst | On Stream Time (hr) | Temp (°C.) | Olefin Percent (%) Carbon Number | | | |
|---|---|---|---|---|---|---|---|
| | | | | 2 | 3 | 4 | 5 |
| 16 | Ru₃(CO)₁₂ | 148.00 | 250 | 0.00 | 38.02 | 44.82 | 24.02 |
| 17 | RuCl₃ | 169.45 | 275 | 25.88 | 47.75 | 56.31 | 60.07 |
| 13 | H₄Ru₄(CO)₁₂ | 72.38 | 250 | 0.00 | 12.63 | 24.65 | 13.53 |
| 12 | H₂FeRu₃(CO)₁₃ | 28.32 | 250 | 0.00 | 16.76 | 26.85 | 14.39 |
| 14 | MnCo(CO)₉ | 24.80 | 275 | 35.12 | 82.18 | 78.56 | 77.17 |

Table XXIX sets out data on MnCo catalysts polymer supported vs. conventionally supported. The conventional catalyst data is from the literature.

TABLE XXIX

Comparison of Polymer Bound and Conventional MnCo Catalysts for
Light Olefins Production from Synthesis Gas

| | Catalyst | | | Reaction | | | Results | |
|---|---|---|---|---|---|---|---|---|
| # | Components | Total Metal Wt % | Mn/Co Ratio | Temp. (°C.) | Press (psig) | Space Velocity (cm³/sec/gm cat.) | CO Conv. (%) | C₂-C₄ Olefin Percent |
| 14 | MnCo(CO)₉—Dipyridyl | 6ᵃ | 1/1ᵃ | 275 | 150 | 7.4 | 20 | 65.57 |
| | MnCo—Al₂O₃ | 27 | 1/2 | 242 | 100 | 0.42 | 36.0 | 0 |
| | MnCo—Al₂O₃ with K₂O | 27 | 1/2 | 279 | 100 | 0.42 | 3.0 | 80.77 |

ᵃEstimated

DEACTIVATION OF CATALYST

The novel catalysts of the invention have demonstrated Fischer-Tropsch activity for extended periods of time (in excess of 200 hours) without significant deactivation. Most significantly, one polymer bound catalyst (Catalyst #6, Table IX) demonstrated increasing activity with time on stream.

Catalyst #16 was submitted for elemental analysis prior and subsequent to the run set out in Table XV. It was determined that ruthenium was not lost during the Fischer-Tropsch reaction. This is very important since the catalyst still contained all of the valuable ruthenium metal. The metal may be recovered by burning the resin.

In the past, only conventional catalysts were used for the vapor phase Fischer-Tropsch reaction. Conventional catalysts generally are supported on either silica or alumina if they are supported at all. They are synthesized by precipitation or fusion techniques and contain no ligand bridges thus making it difficult to obtain small metal clusters which are desired for the Fischer-Tropsch reaction.

It is clear from these results that the catalytic system of the invention is sensitive and that the exact constitution thereof is critical in obtaining the desired results.

The instant invention provides a significant advance in the Fischer-Tropsch reaction since the reaction conditions are mild and the resultant products are not contaminated with catalyst. This invention being thus described, it will be obvious that the same may be varied in many ways. Such variations are not to be regarded as a departure from the scope of the invention, and all such modifications are intended to be included within the scope of the following claims.

What we claim is:

1. In a process for the conversion of synthesis gas to hydrocarbons which comprises contacting said synthesis gas with a catalyst in the vapor phase at a temperature from 175° C. to 300° C. and a pressure of at least 1000 kPa, the improvement comprising using as said catalyst a catalyst represented by the structural formula:

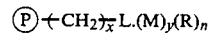

wherein
ⓅⒹ represents a crosslinked macroreticular polystyrene resin which has a crosslink density of at least 5%;
x is 0 or 1;
L represents a ligand selected from the group consisting of bipyridyl, 2-aminopyridine, 2-amino phenol, 2-imino pyridine, sodium anthranilate and potassium anthranilate;
y is an integer from 1 through 8;
when y equals 1, M represents a Group VIII metal from the Periodic Table and when y is from 2 through 8, M represents one or more metals selected from the group consisting of Group VIII metals of the the Periodic Table, manganese, potassium and sodium; with the proviso that at least one M is a Group VIII metal;
R represents the same or different radical selected from the group consisting of hydrogen, carbonyl and halogen; and n represents an integer from 3 through 24.

2. A process according to claim 1 wherein L is dipyridyl and (M)ᵧ(R)ₙ is Ru₃(CO)₁₂.

3. A process according to claim 1 characterized in that L is 2-amino phenol and (M)ᵧ(R)ₙ is H₂FeOs₃(CO)₁₃.

4. A process according to claim 1 characterized in that the temperature is from 225° C. to 250° C.

* * * * *